(12) United States Patent
Naqvi

(10) Patent No.: US 9,414,803 B1
(45) Date of Patent: Aug. 16, 2016

(54) ELECTRONIC STETHOSCOPE DEVICE

(71) Applicant: Tehseen Naqvi, East Northport, NY (US)

(72) Inventor: Tehseen Naqvi, East Northport, NY (US)

( * ) Notice: Subject to any disclaimer, the term of this patent is extended or adjusted under 35 U.S.C. 154(b) by 0 days.

(21) Appl. No.: 14/711,038

(22) Filed: May 13, 2015

(51) Int. Cl.
*A61B 7/04* (2006.01)
*H04W 4/00* (2009.01)

(52) U.S. Cl.
CPC . *A61B 7/04* (2013.01); *H04W 4/008* (2013.01)

(58) Field of Classification Search
None
See application file for complete search history.

(56) References Cited

U.S. PATENT DOCUMENTS

| 3,247,324 | A | 4/1966 | Cefaly et al. | |
|---|---|---|---|---|
| D207,616 | S | 5/1967 | King | |
| 6,533,736 | B1 * | 3/2003 | Moore | A61B 7/04 181/131 |
| 8,396,228 | B2 * | 3/2013 | Bilan | A61B 7/04 181/131 |
| 2001/0050992 | A1 * | 12/2001 | Carman | A61B 7/04 381/67 |
| 2004/0223621 | A1 * | 11/2004 | Orten | A61B 7/04 381/67 |
| 2007/0106179 | A1 * | 5/2007 | Bagha | A61B 7/04 600/586 |
| 2009/0060215 | A1 * | 3/2009 | Ocasio | A61B 7/04 381/67 |
| 2011/0096936 | A1 * | 4/2011 | Gass | A61B 7/04 381/67 |
| 2011/0190665 | A1 * | 8/2011 | Bedingham | A61B 7/04 600/586 |
| 2012/0310115 | A1 * | 12/2012 | Bedingham | A61B 7/04 600/586 |
| 2014/0270218 | A1 * | 9/2014 | Wang | A61B 7/04 381/67 |

* cited by examiner

*Primary Examiner* — Brenda Bernardi
(74) *Attorney, Agent, or Firm* — Crossley and Stevenson Intellectual Property Law

(57) ABSTRACT

The electronic stethoscope device has a Medical Acoustic Collector (MAC) used to auscultate a patient. The MAC microphone communicates with a bio-signal filter/amplifier that communicates with a transmitter. A plurality of separable auditory implements includes earbuds and an earpiece. Each of the earbuds and the earpiece are removably docked within the MAC. The auditory implements communicate with the MAC via a Wireless Personal Area Network (WPAN) which includes but is not limited to a Bluetooth® an Infrared Data Acquisition, and a Body Area Network. The device also selectively communicates with existing wireless media capable devices.

18 Claims, 6 Drawing Sheets

ELECTRONIC STETHOSCOPE DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Of the various types of stethoscopes known in the prior art, few are electronic. Some electronic stethoscopes have digital readouts while others offer separate auscultation devices and earpieces. What has been needed is an electronic stethoscope device that provides completely separate auscultation from audible information derived from a patient. The device should operate via communication pathways that are wireless. The device should provide one-piece storage, and the device should ideally provide more than one auditory implement in receipt of the auscultation.

FIELD OF THE INVENTION

The present electronic stethoscope device relates to stethoscopes and more especially to an electronic stethoscope device that provides separate members for auscultation and audible play that are in wireless communication.

SUMMARY OF THE INVENTION

The general purpose of the electronic stethoscope device, described subsequently in greater detail, is to provide an electronic stethoscope device that has many novel features that result in an electronic stethoscope device which is not anticipated, rendered obvious, suggested, or even implied by prior art, either alone or in combination thereof.

To accomplish this, the electronic stethoscope device has a medical acoustic collector, hereinafter named MAC, having a larger torus and a smaller torus spaced apart from the larger torus by a substantially hollow central member. The smaller torus has an interior surface and an exterior surface spaced apart from the interior surface. A microphone is disposed within the central member. A bio-signal filter/amplifier is disposed within the central member. The bio-signal filter/amplifier is in operational communication with the microphone.

At least one receptacle is disposed within the MAC. One receptacle is selectively disposed through the smaller torus and within the central member proximal the smaller torus. Further, at least one receptacle is selectively disposed within the central member. Each receptacle has a Universal Serial Bus, hereinafter named USB, is disposed within the exterior surface. An indicator light is disposed within the exterior surface. An on/off button is disposed within the exterior surface. The on/off button is in operational communication with the indicator light. A first power source is disposed within the smaller torus. The first power source is in operational communication with the USB, the microphone, the indicator light, the on/off button, and the bio-signal filter/amplifier. A plurality of first charging contacts is disposed within the interior surface. The first charging contacts are in operational communication with the first power source. An alignment protrusion is disposed on the interior surface.

A plurality of auditory implements are provided. One type of auditory implement is an earpiece. Another type of auditory implement provided is at least one earbud. In the art, and earbud is typically defined as a very small insert worn within the ear, an insert that more resembles a hearing aid than an earpiece. An earpiece is typically defined as a visually obvious auditory implement that is much larger than an earbud. Such qualifying differences will be adhered to within. The provided earpiece has a nipple end affixed to an oblate spheroid housing. The nipple end is selectively fitted within the receptacle. The housing has an alignment notch selectively fitted to the protrusion. A plurality of second charging contacts is selectively fitting against the plurality of first charging contacts. An on/off indicator light is disposed within the earpiece. A second power source is in operational communication with the on/off indicator light, and the plurality of second charging contacts.

A Wireless Personal Area Network, hereinafter named WPAN is provided. The WPAN has a transmitter disposed within the MAC. The transmitter is in operational communication with the on/off button. A receiver/amplifier is disposed within the earpiece. A speaker is disposed within the nipple end. The speaker is in operational communication with the receiver/amplifier.

In use, the MAC first power source is charged via the USB. A user then turns the on/off button on and removes the earpiece from the receptacle. Switching the on/off button to an on position also turns on the earpiece via the WPAN. The user can also remove the earpiece prior to switching on the on/off button. The plurality of first charging contacts the plurality of second charging contacts with the earpiece selectively inserted into the receptacle. Upon introduction of the MAC to a patient, the microphone picks up auscultation information which is filtered and amplified by the bio-signal filter/amplifier and transferred to the transmitter. The MAC relays the patient's auscultation information to the earpiece receiver/amplifier. From the receiver/amplifier the information is played through the speaker.

Of note is that other appropriately wireless capable devices such as an existing computer and an existing cellphone, as example, can take part in WPAN communication. Also, an optional earpiece with more than one removable earbud is provided. Each earbud has a second power source within. Each earbud removably plugs into a receptacle on the differing earpiece for charging of the second power source. The earbuds are substantially typical to those in the art as each has a power source, a receiver and a speaker. A plurality of earbuds and the differing earpiece enable a plurality of users to audibly access the patient's auscultation information simultaneously. More than one practitioner can therein listen to vitals. A second earbud is also valuable for training purposes. The WPAN selectively employs but is not limited to a Bluetooth®, an Infrared Data Association, hereinafter named IrDA, and a Body Area Network, hereinafter named BAN, which is based on IEEE 902.15.6 standard for transmission via the capacitive near field of human skin allowing near field communication of devices worn by and near a wearer. The device provides audible auscultation far superior to that provided by a typical, long-known one piece stethoscope.

Thus has been broadly outlined the more important features of the present electronic stethoscope device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
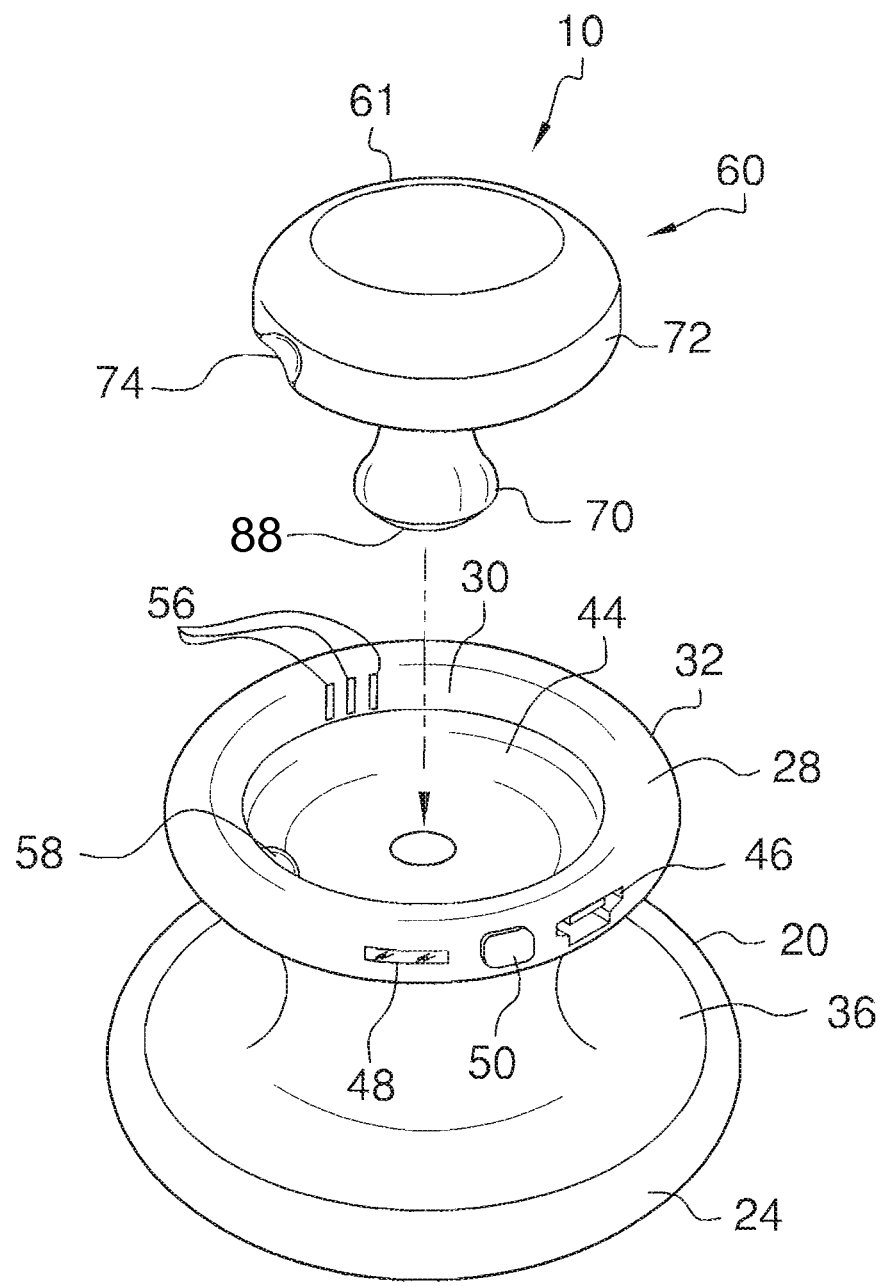
FIG. 1 is a perspective view.
Figure 2:
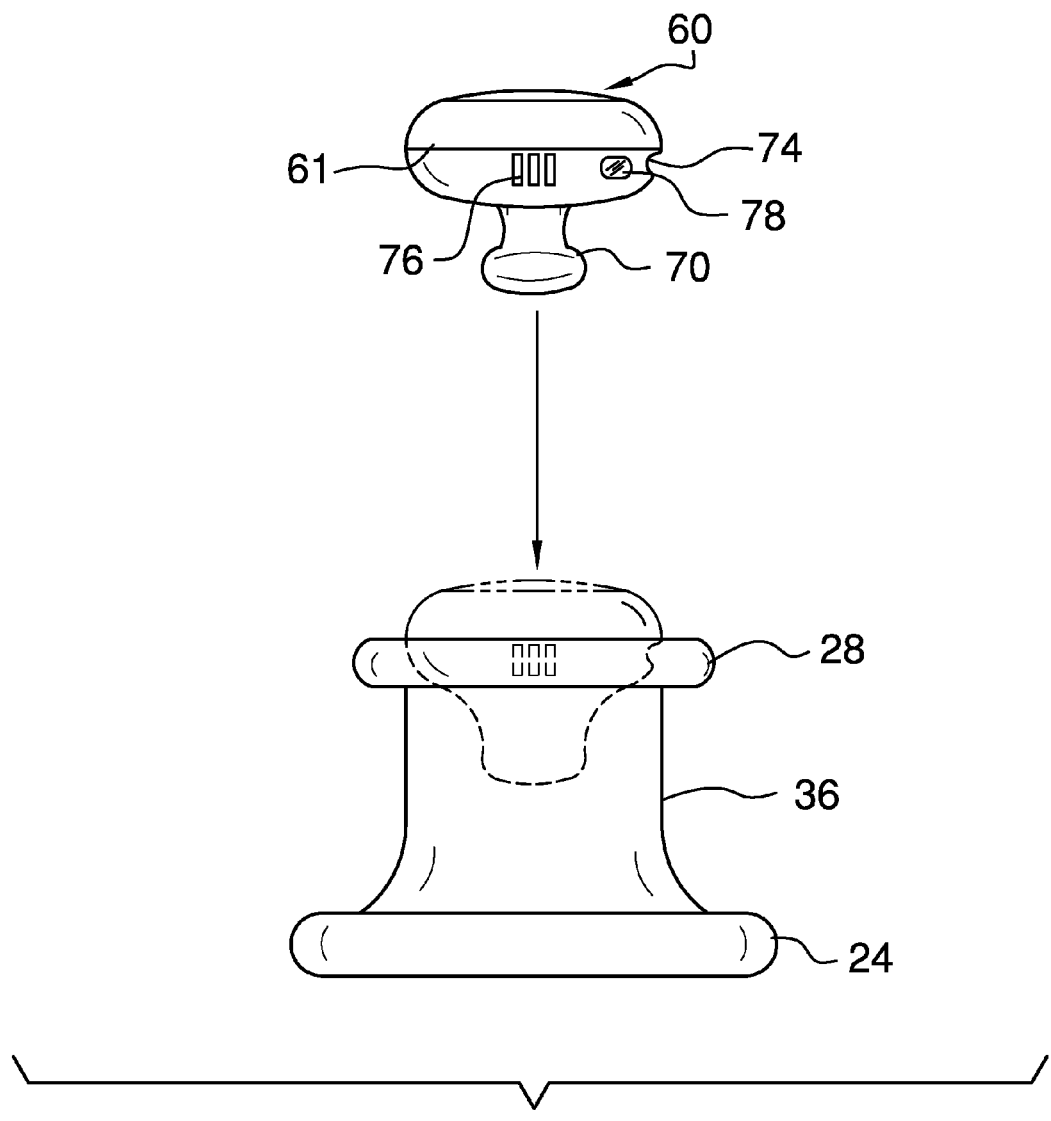
FIG. 2 is a lateral elevation view.
Figure 3:
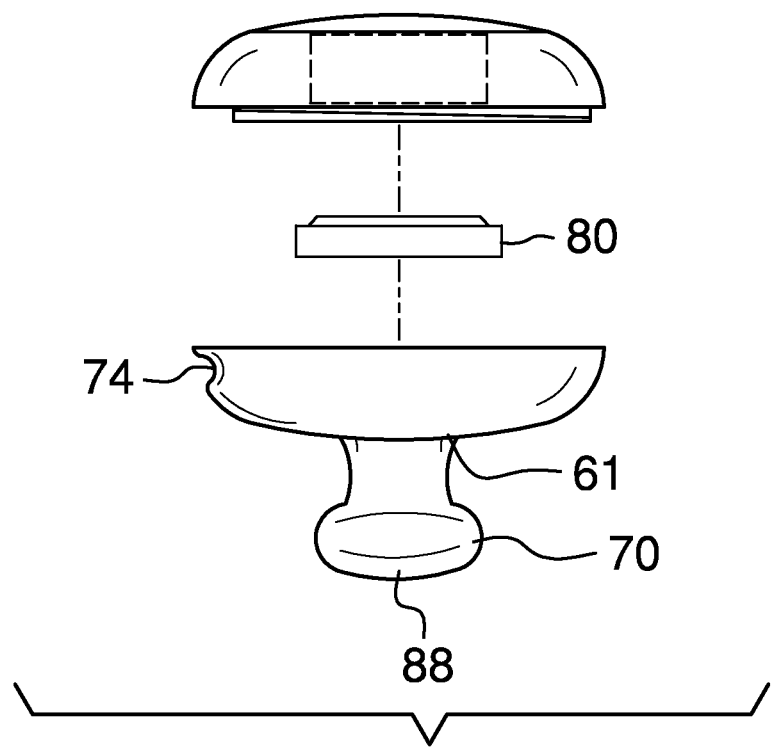
FIG. 3 is a lateral view of a disassembled earpiece.
Figure 4:
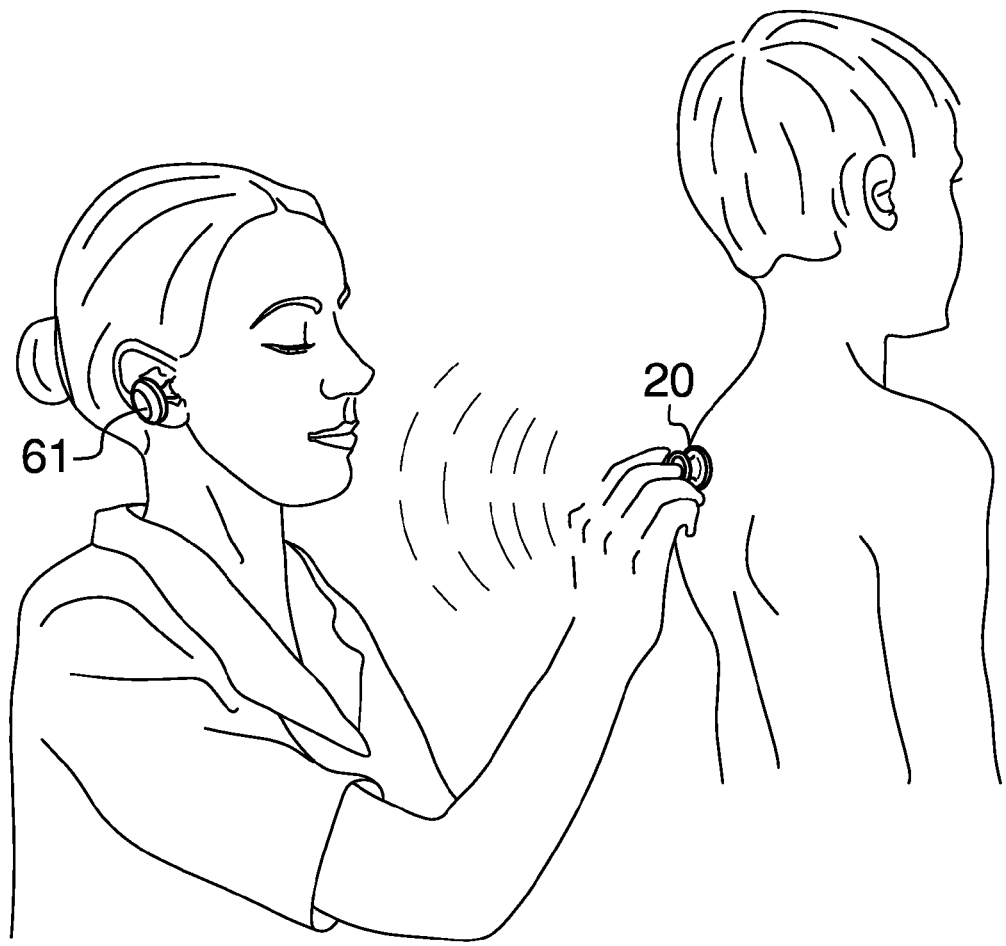
FIG. 4 is an in use view.
Figure 5:
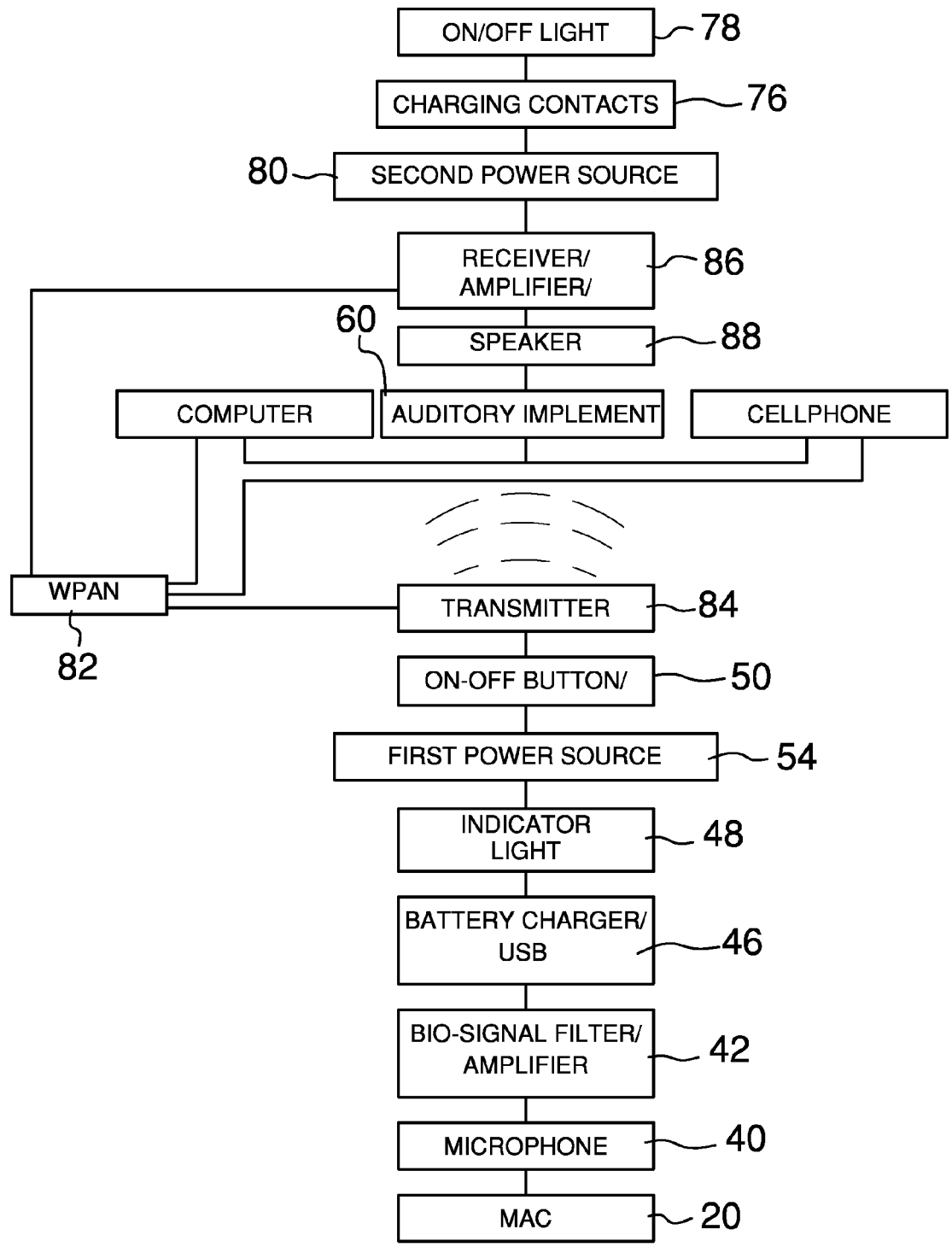
FIG. 5 is a block diagram.
Figure 6:
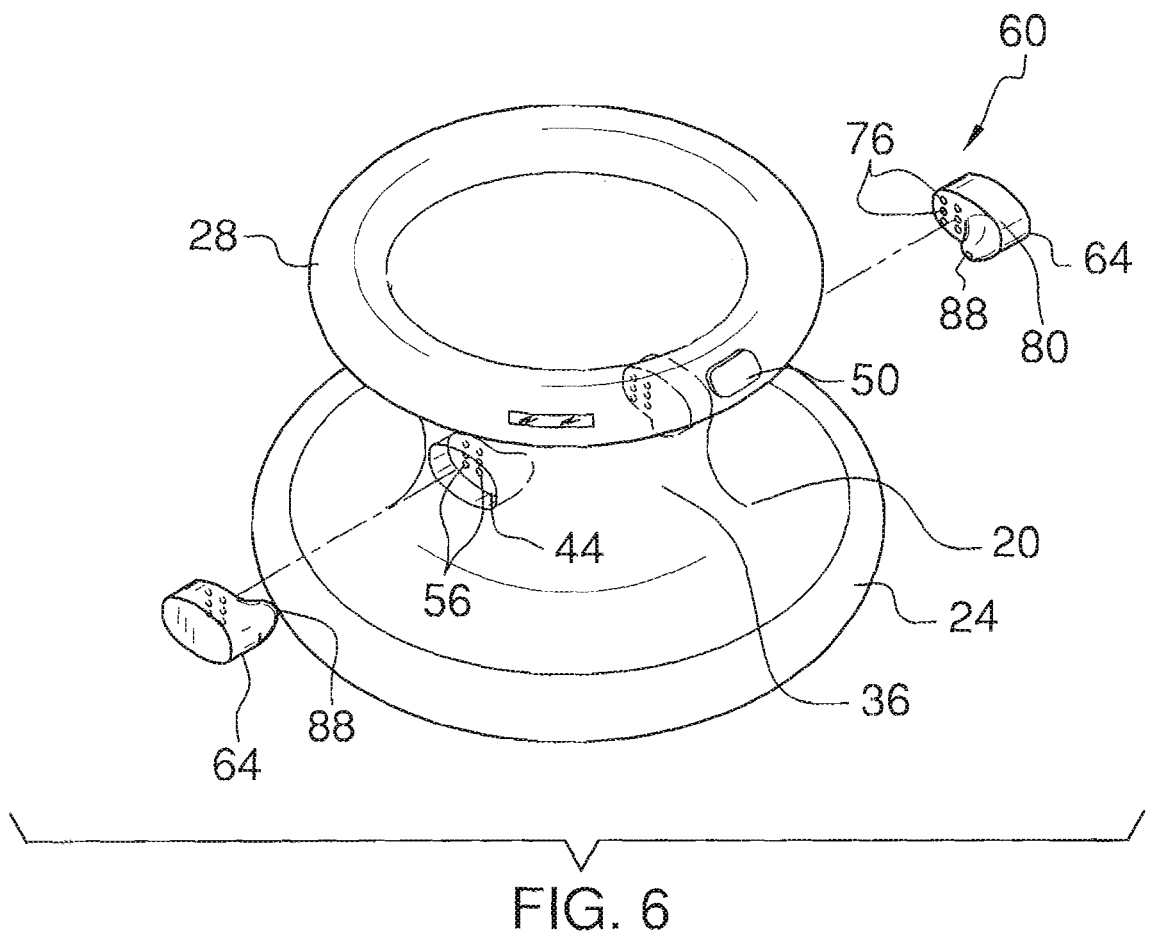
FIG. 6 is a perspective view of an optional earpiece.

With reference now to the drawings, and in particular FIGS. 1 through 6 thereof, an example of the electronic stethoscope device employing the principles and concepts of the present electronic stethoscope device and generally designated by the reference number 10 will be described.

Referring to FIGS. 1 through 6, the electronic stethoscope device 10 has a medical acoustic collector (MAC) 10 having a larger torus 24 and a smaller torus 28 spaced apart from the larger torus 24 by a substantially hollow crateriform shaped central member 36. The smaller torus 28 has an interior surface 30 and an exterior surface 32 spaced apart from the interior surface 30. A microphone 40 is disposed within an interior diameter of the central member 36. A bio-signal filter/amplifier 42 is disposed within the central member 36. The bio-signal filter/amplifier 42 is in operational communication with the microphone 40. A transmitter 84 is disposed within the MAC 20.

At least one receptacle 44 is disposed within the MAC 20. On receptacle 44 is disposed through the smaller torus 28 and within the central member 36 proximal the smaller torus 28. A USB 46 is disposed within the exterior surface 32. An indicator light 48 is disposed within the exterior surface 32. An on/off button 50 is disposed within the exterior surface 32. The on/off button 50 is in operational communication with the indicator light 48. A first power source 54 is disposed within the MAC 20. The first power source 54 is in operational communication with the USB 46, the indicator light 48, the on/off button 50, the microphone, the transmitter 84, and the bio-signal filter/amplifier 42. With the receptacle 44 disposed through the smaller torus, a plurality of first charging contacts 56 is disposed within the interior surface 30. The first charging contacts 56 are in operational communication with the first power source 54. With the receptacle 44 disposed through the smaller torus, an alignment protrusion 58 is disposed on the interior surface 30.

Of a plurality of provided auditory implements 60, one auditory implement 60 is an earpiece 61 having a nipple end 70 affixed to an oblate spheroid housing 72. A speaker 88 is disposed within the nipple end 70. A receiver/amplifier 86 is disposed within the earpiece 61. The nipple end 70 is selectively fitted within the receptacle 44. With the earpiece 61, the housing 72 has an alignment notch 74 selectively fitted to the protrusion 58. A plurality of second charging contacts 76 of the earpiece 61 selectively fits against the plurality of first charging contacts 56. An on/off indicator light 78 is disposed within the earpiece 61. The second power source 80 is in operational communication with the on/off indicator light 78, the speaker 88, the receiver/amplifier 86, and the plurality of second charging contacts 76.

Of the plurality of auditory implements 60, at least one earbud 64 is provided. With the earbud 64 provided device 10, at least one receptacle 44 having a plurality of second charging contacts 76 is provided within the central member 36. Each earbud contains one speaker 88 and the receiver/amplifier 86. Each earbud 64 contains the second power source 80 in operational communication with the speaker, the second charging contacts, and the receiver/amplifier 86.

A Wireless Personal Area Network (WPAN) 82 is provided. The WPAN 82 comprises the transmitter 84 and a receiver/amplifier 86 disposed within the earpiece 61 and within each earbud 64. The speaker 88 is in operational communication with the receiver/amplifier 86 and the second power source 80.

In use with the earpiece 61 equipped device 10, the MAC 20 first power source 54 is charged via the USB 46. A user then turns the on/off button 50 on and removes the earpiece 61 from the receptacle 44. Switching the on/off button 50 to an on position turns on the MAC 20 and the earpiece 61 via the WPAN 82. The user can also remove the earpiece 61 prior to switching on the on/off button 50. The plurality of first charging contacts 56 contacts engage the plurality of second charging contacts 76 with the earpiece 61 selectively inserted into the receptacle 44. Upon introduction of the MAC 20 to a patient, the microphone 40 picks up auscultation which is filtered and amplified by the bio-signal filter/amplifier 42 and transferred to the transmitter 84. The WPAN 82 relays the patient's auscultation to the receiver/amplifier 86. From the receiver/amplifier 86 the auscultation is played through the speaker 88.

In use with the earbud 64 equipped device 10, the MAC 20 first power source 54 is charged via the USB 46. A user then turns the on/off button 50 on and removes the earbuds 64 from the receptacles 44 as chosen. Switching the on/off button 50 to an on position turns on the MAC 20 and the earbud 64 via the WPAN 82. The user can also remove the earbud 64 prior to switching on the on/off button 50. The plurality of first charging contacts 56 contacts the plurality of second charging contacts 76 with the earbud 64 selectively inserted into the receptacle 44. Upon introduction of the MAC 20 to a patient, the microphone 40 picks up auscultation which is filtered and amplified by the bio-signal filter/amplifier 42 and transferred to the transmitter 84. The WPAN 82 relays the patient's auscultation to the receiver/amplifier 86. From the receiver/amplifier 86 the auscultation is played through the speaker 88.

Of note is that other appropriately configured wireless capable devices such as an existing computer and an existing cellphone, for example, selectively take part in WPAN 82 communication. The WPAN 82 selectively employs but is not limited to Bluetooth®, Infrared Data Association (IrDA), and a Body Area Network (BAN) which is based on Institute of Electronics and Electrical Engineers (IEEE) 902.15.6 standard for transmission via the capacitive near field of human skin allowing near field communication of devices worn by and near a wearer.

What is claimed is:
1. An electronic stethoscope device comprising:
 a medical acoustic collector (MAC) having a larger torus and a smaller torus spaced apart from the larger torus by a substantially hollow central member, the smaller torus having an interior surface and an exterior surface spaced part from the interior surface;
 a microphone disposed within an inner diameter of the larger torus;
 a bio-signal filter/amplifier disposed within the central member, the bio-signal filter/amplifier in operational communication with the microphone;

a transmitter disposed within the central member, the transmitter in operational communication with the bio-signal filter/amplifier;
at least one receptacle disposed within the central member;
a universal serial bus (USB) disposed within the exterior surface;
an indicator light disposed within the exterior surface;
an on/off button disposed within the exterior surface, the on/off button in operational communication with the indicator light;
a first power source disposed within the MAC, the first power source in operational communication with the USB, the indicator light, the on/off button, the microphone, the bio-signal filter/amplifier, the transmitter;
a plurality of first charging contacts disposed within the MAC, the first charging contacts in operational communication with the first power source;
at least one auditory implement, the implement having:
    a plurality of second charging contacts selectively fitted against the plurality of first charging contacts;
    a second power source in operational communication with the on/off indicator light, the plurality of second charging contacts;
    a receiver/amplifier in operational communication with the second power source;
    a speaker in operational communication with the receiver/amplifier;
a wireless personal area network (WPAN) comprising:
    the transmitter; and
    the receiver/amplifier.

2. The electronic stethoscope device of claim 1 wherein the WPAN partially comprises a Bluetooth.

3. The electronic stethoscope device of claim 1 wherein the WPAN partially comprises an infrared data association (IrDA).

4. The electronic stethoscope device of claim 1 wherein the WPAN partially comprises a body area network (BAN).

5. The electronic stethoscope device of claim 2 wherein the WPAN comprises a plurality of existing WPAN capable devices.

6. The electronic stethoscope device of claim 3 wherein the WPAN comprises a plurality of existing WPAN capable devices.

7. The electronic stethoscope device of claim 4 wherein the WPAN comprises a plurality of existing WPAN capable devices.

8. An electronic stethoscope device comprising:
medical acoustic collector (MAC) having a larger torus and a smaller torus spaced apart from the larger torus by a substantially hollow central member having a crateriform shape, the smaller torus having an interior surface and an exterior surface spaced apart from the interior surface;
a microphone disposed within an interior diameter of the larger torus;
a bio-signal filter/amplifier disposed within the central member, the bio-signal filter/amplifier in operational communication with the microphone;
a transmitter disposed within the MAC, the transmitter in operational communication with the bio-signal filter/amplifier, an on/oil button;
a receptacle disposed through the smaller torus and within the central member proximal the smaller torus;
a universal serial bus (USB) disposed within the exterior surface;
an indicator light disposed within the exterior surface;
the on/off button disposed within the exterior surface, the on/off button in operational communication with the indicator light;
a first power source disposed within the MAC, the first power source in operational communication with the USB, the indicator light, the on/off button, the microphone, the bio-signal filter/amplifier, the transmitter;
a plurality of first charging contacts disposed within the interior surface, the first charging contacts in operational communication with the first power source;
a protrusion disposed on the interior surface;
an auditory implement comprising an earpiece, the earpiece having a nipple end affixed to an oblate spheroid shaped housing, the nipple end selectively fitted within the receptacle, the housing having:
    an alignment notch selectively fitted to the protrusion;
    a plurality of second charging contacts selectively fitting against the plurality of first charging contacts;
    an on/off indicator light;
    a receiver/amplifier;
    a speaker in operational communication with the receiver/amplifier;
    a second power source in operational communication with the indicator light; the on/off indicator light, the plurality of second charging contacts, the receiver/amplifier, the speaker;
a wireless personal area network (WPAN) comprising:
    the transmitter; and
    the receiver/amplifier.

9. The electronic stethoscope device of claim 8 wherein the WPAN partially comprises a Bluetooth.

10. The electronic stethoscope device of claim 8 wherein the WPAN partially comprises an infrared data association (IrDA).

11. The electronic stethoscope device of claim 8 wherein the WPAN partially comprises a body area network (BAN).

12. The electronic stethoscope device of claim 9 wherein the WPAN further comprises a plurality of existing WPAN capable devices.

13. The electronic stethoscope device of claim 10 wherein the WPAN further comprises a plurality of existing WPAN capable devices.

14. The electronic stethoscope device of claim 11 wherein the WPAN further comprises a plurality of existing WPAN capable devices.

15. An electronic stethoscope device comprising:
a medical acoustic collector (MAC) having a larger torus and a smaller torus spaced apart from the larger torus by a substantially hollow central member having a crateriform shape, the smaller torus having an interior surface and an exterior surface spaced apart from the interior surface;
a microphone disposed within an interior diameter of the larger torus;
a bio-signal filter/amplifier disposed within the central member, the bio-signal filter/amplifier in operational communication with the microphone;
a transmitter disposed within the MAC, the transmitter in operational communication with the bio-signal filter/amplifier, the on/off button;
at least one receptacle disposed within the central member;
a universal serial bus (USB) disposed within the exterior surface;
an indicator light disposed within the exterior surface;
an on/off button disposed within the exterior surface, the on/off button in operational communication with the indicator light;

a first power source disposed within the MAC, the first power source in operational communication with the USB, the indicator light, the on/off button, the microphone, the bio-signal filter/amplifier, the transmitter;

a plurality of first charging contacts disposed within the receptacle, the first charging contacts in operational communication with the first power source;

an auditory implement comprising: an earbud, the earbud having
- a plurality of second charging contacts selectively fitted to the plurality of first charging contacts;
- an on/off indicator light;
- a receiver/amplifier;
- a speaker in operational communication with the receiver/amplifier;
- a second power source in operational communication with the plurality of second charging contacts, the indicator light, the on/off indicator light, the receiver/amplifier, the speaker;

a wireless personal area network (WPAN) comprising:
- the transmitter; and
- the receiver/amplifier.

16. The electronic stethoscope device of claim 15 wherein the WPAN partially comprises but is not limited to a list of wireless communications comprising a Bluetooth, an infrared data association (IrDA), a body area network (BAN).

17. The electronic stethoscope device of claim 15 wherein the WPAN further comprises a plurality of existing WPAN capable devices.

18. The electronic stethoscope device of claim 16 wherein the WPAN further comprises a plurality of existing WPAN capable devices.

\* \* \* \* \*